United States Patent
Kim et al.

(10) Patent No.: US 12,214,215 B2
(45) Date of Patent: Feb. 4, 2025

(54) STIMULATING DEVICE FOR GROWTH PLATE

(71) Applicant: SOLAR LUCE CO., LTD., Pyeongtaek-si (KR)

(72) Inventors: Yong-Il Kim, Seongnam-si (KR); Jongwook Kim, Seongnam-si (KR); Jae Young Kim, Seoul (KR); Ba Wool Kim, Hwaseong-si (KR)

(73) Assignee: SOLAR LUCE CO., LTD., Pyeongtaek-si (KR)

( * ) Notice: Subject to any disclaimer, the term of this patent is extended or adjusted under 35 U.S.C. 154(b) by 224 days.

(21) Appl. No.: 17/414,326

(22) PCT Filed: Dec. 10, 2019

(86) PCT No.: PCT/KR2019/017336
§ 371 (c)(1),
(2) Date: Jun. 16, 2021

(87) PCT Pub. No.: WO2020/130453
PCT Pub. Date: Jun. 25, 2020

(65) Prior Publication Data
US 2022/0072331 A1 Mar. 10, 2022

(30) Foreign Application Priority Data

Dec. 20, 2018 (KR) .................. 10-2018-0166784

(51) Int. Cl.
*A61N 5/06* (2006.01)
*A61H 23/02* (2006.01)
(52) U.S. Cl.
CPC .......... *A61N 5/0613* (2013.01); *A61H 23/02* (2013.01); *A61H 2201/10* (2013.01);
(Continued)

(58) Field of Classification Search
CPC .......... A61N 5/0613; A61N 2005/0645; A61N 2005/0659; A61N 5/06; A61N 2005/0663;
(Continued)

(56) References Cited

U.S. PATENT DOCUMENTS 7,503,927 B1 * 3/2009 Vetanze ................. A61N 1/322
607/152
2006/0271131 A1 * 11/2006 Passy .................. A61N 5/0613
607/94
(Continued)

FOREIGN PATENT DOCUMENTS

KR 10-0975595 B1 8/2010
KR 20140024612 A * 8/2012 ........... A61H 33/067
(Continued)

OTHER PUBLICATIONS

KR101773785B1 machine translation of written description and claims. (Year: 2017).*
(Continued)

*Primary Examiner* — Michael R Reid
*Assistant Examiner* — Tyler A Raubenstraw
(74) *Attorney, Agent, or Firm* — Revolution IP, PLLC (57) ABSTRACT

A light source unit not only applies red light and infrared light to promote immediate cellular activity, but also applies the light to a femoral epiphysis area (first area) and a tibial epiphysis area (second area) together so that a stimulating device for a growth plate includes a light source unit that directly emits light of 600 to 1100 nm to a femoral epiphysis area (first area) and a tibial epiphysis area (second area) where the growth plates are distributed.

11 Claims, 6 Drawing Sheets

(52) U.S. Cl.
CPC .. *A61H 2201/164* (2013.01); *A61H 2201/165* (2013.01); *A61N 2005/0645* (2013.01); *A61N 2005/0659* (2013.01); *A61N 2005/0663* (2013.01)

(58) Field of Classification Search
CPC ........ A61N 5/0616; A61N 5/00; A61H 23/02; A61H 2201/10; A61H 3/00; A61H 2201/164; A61H 2201/165; A61H 2205/10; A61H 2205/106
See application file for complete search history.

(56) References Cited

U.S. PATENT DOCUMENTS

| | | | |
|---|---|---|---|
| 2011/0060254 A1 | 3/2011 | Yoon et al. | |
| 2011/0144727 A1* | 6/2011 | Benedict | A61N 5/0613 607/91 |
| 2011/0251659 A1* | 10/2011 | Prescott | A61N 5/0616 607/90 |
| 2011/0301673 A1* | 12/2011 | Hoffer | A61N 5/0613 607/91 |
| 2013/0079759 A1* | 3/2013 | Dotson | A61N 5/0613 606/4 |
| 2013/0289670 A1* | 10/2013 | Thiberg | A61N 5/06 607/88 |
| 2013/0304019 A1* | 11/2013 | Cooper | A61N 5/062 604/20 |
| 2013/0310719 A1* | 11/2013 | Davis | A61H 9/0085 601/149 |
| 2014/0209594 A1* | 7/2014 | Besner | A61F 7/007 219/217 |
| 2014/0277298 A1* | 9/2014 | Tapper | A61N 5/0616 607/91 |
| 2015/0246240 A1* | 9/2015 | Huttemann | A61N 5/06 607/89 |
| 2016/0030281 A1* | 2/2016 | Shafieloo | A61H 23/0245 601/48 |
| 2017/0014640 A1* | 1/2017 | Kariguddaiah | A61F 5/0118 |
| 2017/0216616 A1* | 8/2017 | Boyajian | A61N 5/062 |
| 2018/0228681 A1* | 8/2018 | Iverson | A61H 1/00 |
| 2018/0360665 A1* | 12/2018 | Melone | A61N 5/0613 |
| 2019/0083808 A1* | 3/2019 | Iverson | A61N 5/0613 |
| 2019/0275347 A1* | 9/2019 | Ouyang | A61N 5/0613 |

FOREIGN PATENT DOCUMENTS

| | | | | |
|---|---|---|---|---|
| KR | 10-1329959 B1 | 11/2013 | | |
| KR | 10-1366485 B1 | 2/2014 | | |
| KR | 101773785 B1 * | 5/2017 | | A61F 7/007 |
| WO | WO-2016209856 A1 * | 12/2016 | | A61N 5/06 |
| WO | WO-2018026680 A1 * | 2/2018 | | A61B 5/02055 |

OTHER PUBLICATIONS

Machine translation of written description and claims for KR20140024612A via espacenet (Year: 2014).*

International Search Report for PCT/KR2019/017336 mailed Mar. 19, 2020 from Korean Intellectual Property Office.

* cited by examiner

STIMULATING DEVICE FOR GROWTH PLATE

CROSS REFERENCE TO PRIOR APPLICATIONS

This application is a National Stage Application of PCT International Patent Application No. PCT/KR2019/017336 filed on Dec. 10, 2019, under 35 U.S.C. § 371, which claims priority to Korean Patent Application No. 10-2018-0166784 filed on Dec. 20, 2018, respectively, which are all hereby incorporated by reference in their entirety.

TECHNICAL FIELD

The present invention relates to a stimulating device for a growth plate, and more particularly, to a stimulating device for a growth plate using light.

BACKGROUND ART

Light therapy is a medical technique used for a long time to treat various diseases. A method of using solar light for treating skin disease was used in Egypt, India and China, thousands of years ago.

A therapy using solar light was re-examined by Niels Ryberg Finsen, as a winner of the Nobel Prize in Medicine in 1903, and then a phototherapy using artificial light begins.

Recently, a method using a LED light source among light sources for treating skin diseases is emerging. The LED light source may effectively treat a disease region having a large area by appropriate light output unlike intensively treating a local area by a high-output laser.

Since the LED light source has a narrow wavelength bandwidth to emit a light source of a specific wavelength, harmful ultraviolet (UV), unnecessary visible light, or the like is not emitted. As a result, there is an advantage of having high energy efficiency and less side effects to damage tissues or eyes due to low energy. Accordingly, the US FDA is permitted to use treatment of using a LED light source of red light and an infrared region to human beings.

As physical characteristics of the LED light source, there are advantages that the life is long and the power consumption is low to be eco-friendly, and a volume is small to facilitate a spatial utilization. However, a light therapy technology that has been developed so far is mostly limited to the skin, and the development of other fields is very lack.

Particularly, there is almost no stimulating device for a growth plate which has been commercialized so far, except for traditional physical massage devices. In addition, theoretically, devices of applying ultrasonic waves and the like have been developed, but it is not commercialized due to side effects such as a hemolytic phenomenon of cells.

That is, in Prior Art 1, there is disclosed a handy type growth accelerating device including ultrasonic waves and an LED device, but there is almost not disclosed light characteristics of the LED. As described above, side effects on growth plate cells when applying the ultrasonic waves becomes a problem, and even in the case, since a user holds the device and needs to directly stimulate the corresponding region of the human body, there is a problem that it is difficult to express a close effect of stimulating the growth plate.

PRIOR ARTS

[Patent Document]
(Patent Document 0001) Korean Patent Registration No. 10-0975595 (Aug. 13, 2010)

DISCLOSURE

Technical Problem

The present invention is to solve the problems in the related art, and an object of the present invention is to provide a stimulating device for a growth plate capable of completely blocking cell side effects and continuously and effectively stimulating the growth plate non-invasively by optimal light.

Technical Solution

According an aspect of the present invention, a stimulating device for a growth plate includes a light source unit which directly emits light of 600 nm to 1100 nm to a femoral epiphysis area (first area) and a tibial epiphysis area (second area) where growth plates are distributed.

The light source unit may include a first module disposed in one side surface of the knee of the first area and the second area and a second module disposed at an opposite side surface to face the first module, wherein light source devices may be disposed in the first module and the second module.

In order to concentrate the light at the growth plates of the first area and the second area, the light source devices may be disposed in the first module and the second module so that the light emission amounts of the upper and lower parts of the first module and the second module are larger than that of the center thereof.

The light source devices may include a visible light emitting device for emitting red light having a wavelength of 600 nm to 730 nm and a non-visible light emitting device for emitting infrared light having a wavelength of 750 nm to 1100 nm together.

The stimulating device for the growth plate may further include a light source unit which emits light to a blood vessel area behind the knee (third area).

The stimulating device for the growth plate may further include a vibration unit which applies vibration to any one of the first area to the third area.

At this time, the vibration unit may be applied to the third area.

The red light and the infrared light may be simultaneously applied to the first area to the third area.

The vibration of the vibration unit and the light emission of the light source unit may be alternately or simultaneously performed.

The vibration unit for applying the vibration to the third area may be formed to connect the first module and the second module. At this time, the stimulating device for the growth plate may be formed so that the front of the knee is opened.

The stimulating device for the growth plate may simultaneously apply the light and the vibration to the first area to the third area.

Advantageous Effects

According to the present invention, the light source unit not only applies red light and infrared light to promote immediate growth plate cell activity, but also applies the light to the femoral epiphysis area (first area), the tibial epiphysis area (second area), and the blood vessel area behind the knee (third area) together to activate the blood flow activities, thereby applying highest efficiency of light required for growth to an optimal position of the human body without cell side effects.

BEST MODE FOR THE INVENTION

Hereinafter, an embodiment of the present invention will be described in detail to be easily implemented by those skilled in the art with reference to the accompanying drawings. The present invention may have various modifications and various embodiments and specific embodiments will be illustrated in the drawings and described in detail. However, the present invention is not limited to specific embodiments, and it should be understood that the present invention covers all the modifications, equivalents and replacements included within the idea and technical scope of the present invention.

Terms including ordinal numbers, such as first and second, are used for describing various constituent elements, but the constituent elements are not limited by the terms. The terms are used only to discriminate one component from the other component.

For example, a first component may be referred to as a second component without departing from the scope of the present invention, and similarly, the second component may be referred to as the first component. A term 'and/or' includes a combination of a plurality of associated disclosed items or any item of the plurality of associated disclosed items.

Unless otherwise defined, all terms used herein including technological or scientific terms have the same meanings as those generally understood by a person with ordinary skill in the art to which the inventions pertain. Terms which are defined in a generally used dictionary should be interpreted to have the same meaning as the meaning in the context of the related art, and are not interpreted as ideal or excessively formal meanings unless otherwise defined in the present application.

Figure 1:
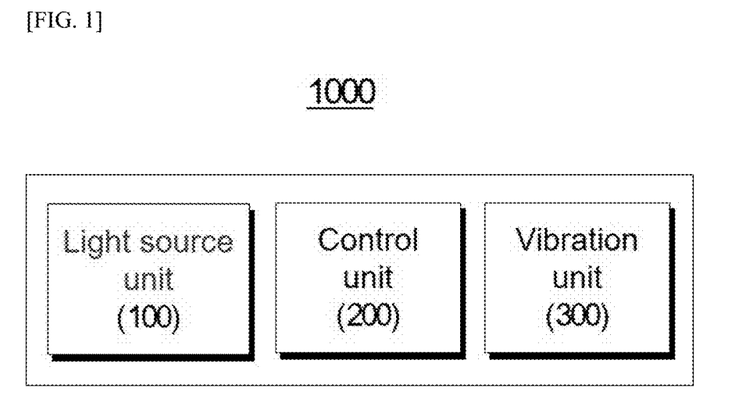
FIG. 1 is a schematic diagram of a stimulating device for a growth plate according to an embodiment of the present invention.
Figure 2:
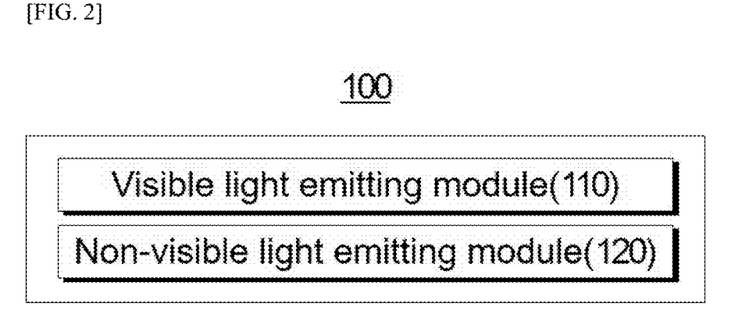
FIG. 2 is a diagram illustrating a light source unit in FIG. 1.
Figure 3:
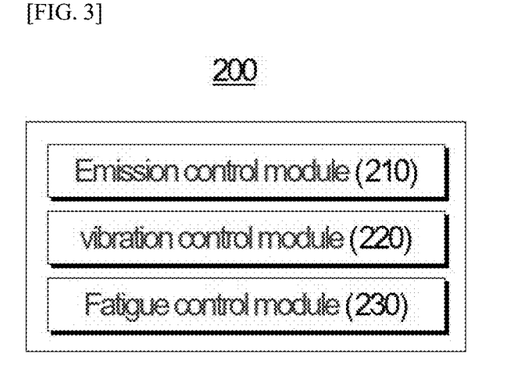
FIG. 3 is a diagram illustrating a control unit in FIG. 1.
Figure 4:
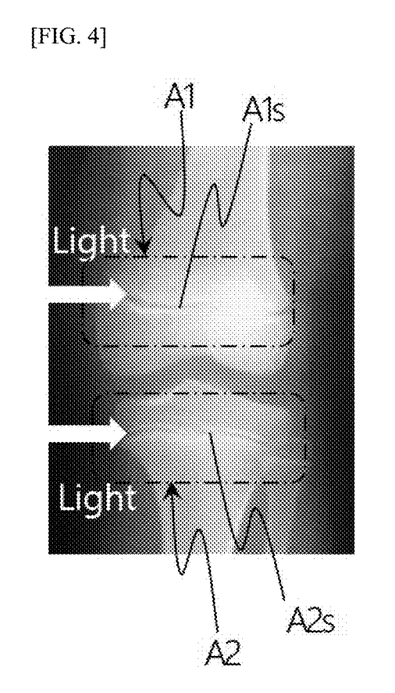
FIG. 4 is a diagram for describing applying light to a first area and a second area.
Figure 5:
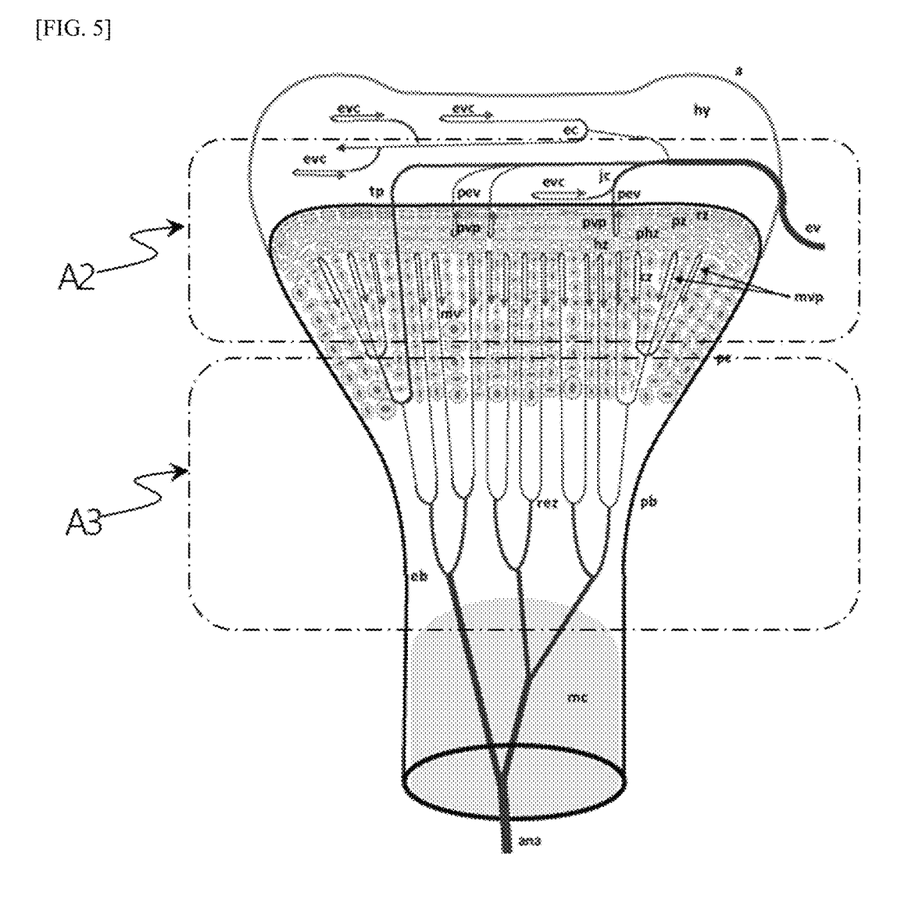
FIG. 5 is a diagram for describing applying light to a second area and a third area.

Hereinafter, a stimulating device for a growth plate according to an embodiment of the present invention will be described. FIG. 1 is a schematic diagram of a stimulating device for a growth plate according to an embodiment of the present invention, FIG. 2 is a diagram illustrating a light source unit in FIG. 1, FIG. 3 is a diagram illustrating a control unit in FIG. 1, FIG. 4 is a diagram for describing applying light to a first area and a second area, and FIG. 5 is a diagram for describing applying light to a second area and a third area.

Referring to the drawings, a stimulating device 1000 for a growth plate according to an embodiment of the present invention may include a light source unit 100 and a control unit 200, and further include a vibration unit 300.

At this time, the light source 100 emits LED light or laser light, and applies the light to at least one of a femoral epiphysis area (first area) A1, a tibial epiphysis area (second area) A2, and a blood vessel area behind the knee A3. Preferably, the light source unit 100 applies the light to the first area A1 and the second area A2 at the same time. In the first area A1 and the second area A2, since the blood vessel area is divided into an upper part and a lower part, an expression balance of growth factors of the upper part and the lower part may be broken when the light is applied only to any one part thereof.

Furthermore, the light source unit 100 may emit the light even to the third area A3 connecting the first area A1 and the second area A2 divided into each other through blood vessel circulation. Since the third area A3 is the blood vessel area behind the knee and connected to the first area A1 and the second area A2, in the case of applying the light to the third area A4 together when applying the light to the first area A1 and the second area A3, the expression frequency of the growth factor is significantly increased. That is, in the case of stimulating particularly a knee growth plate among the growth plates, it is most preferred that the femoral epiphysis area as the first area and the tibial epiphysis area as the second area are simultaneously stimulated and the blood vessel area behind the knee connected to both areas is simulated at the same time.

Meanwhile, the light source unit 100 consists of a visible light emitting device 110 and a non-visible light emitting device 120. In the prior art described in the related art, there is disclosed that it is advantageous to use infrared light having a very deep skin penetration depth. In the case of continuously applying the infrared light to growth plate cells alone, it is not preferred that photoinhibition is deepened. In addition, when the red visible light is used, an activation effect of the cartilage, which is a component of the growth plate, is further enhanced. Accordingly, the stimulating device for the growth plate according to an embodiment of the present invention may reinforces cell recovery and regeneration functions and more effectively stimulate the growth plates by using both the infrared light and the red visible light.

Accordingly, the light source unit according to an embodiment of the present invention further includes a visible light emitting device 110 emitting red light, wherein the red light is emitted at 630 nm to 730 nm.

When the light of 630 nm to 730 nm is emitted to the skin, the light is absorbed into the mitochondria to promote ATP generation and promote intracellular energy metabolism, thereby promoting cell growth and cell regeneration. However, since a lot of light is absorbed in hemoglobin that is mainly distributed in vascular cells, there is a difficulty in photon transfer into deeper growth plate cells in a region of a lot of blood vessels.

However, the light source unit 100 according to an embodiment of the present invention is attached to the knee, in which a depth to the knee joint and the cartilage where the growth plate is disposed is jut about 5 mm and photoinhibition by hemoglobin is shown therein at a very small frequency unlike other regions of the human body. Therefore, the red light having a minimum wavelength in the vicinity of 630 nm also sufficiently reaches the cartilage growth plate like infrared light.

Further, the light source unit 100 according to an embodiment of the present invention may further emit light of 750 nm to 900 nm. This is to activate the cartilage cells of the growth plate and directly stimulate the blood vessel connected with the growth plate and the blood vessel area behind the knee. That is, when infrared light at the wavelength range is applied, the infrared light may be deeply penetrate while completely blocking absorption interference of the hemoglobin described above and directly stimulate the growth plate cells, thereby further enhancing the growth factor expression frequency.

When a wavelength in the range is emitted together, a complex IV (cytochrome c oxidase) acts as a photo-receptor in a mitochondria respiratory chain in the cells to promote the ATP generation. In addition, a secondary cell message signaling pathway is initiated, and as a result, the energy metabolism is activated and the cell viability is increased, thereby preventing the apoptosis of the ischemic region and enhancing a neuronal regeneration mechanism.

This mechanism promotes the cell growth and the cell regeneration and affects even undifferentiated mesoderm cells to be differentiated into osteoblasts and bone cells which are growth plate cells to have a useful function for regeneration of bone tissue. As a result, the generation of collagen, which is a cartilage material, is promoted, and the differentiation of the osteoblasts and bone cells is promoted to induce direct growth.

As such, in the stimulating device for the growth plate according to the present invention, the light source unit not only applies red light and infrared light to promote immediate growth plate cell activity, but also applies the light to the femoral epiphysis area (first area), the tibial epiphysis area (second area), and the blood vessel area behind the knee (third area) together, thereby applying highest efficiency of light required for growth to an optimal position of the human body.

Meanwhile, the stimulating device 1000 for the growth plate according to an embodiment of the present invention may further include a vibration unit 300 for applying vibration to any one of the first area A1 to the third area A3. More preferably, the light source unit 100 applies the aforementioned light to the entire first area A1 to the third area A3 and preferably, the vibration unit 300 applies the vibration to the third area A3. Since the first area A1 and the second area A2 correspond to the sides of the knee, an effect of applying the vibration to the growth plate cells is slight as joint blocks, and the third area A3 has a large blood vessel distribution due to a relatively large skin, so that the vibration in continuous waves or pulse waves stimulates the cells in the blood vessel. In this case, the vibration application to the vibration unit 300 may be performed alternately or simultaneously with the light emission of the light source unit. That is, appropriate physical stimuli are added to exhibit a growth promoting effect due to more efficient blood flow improvement.

To this end, the control unit 200 includes an emission control module 21 and a vibration control module 220 and may further include a fatigue control module 230 which controls the entire driving by measuring the cell activation and the cell fatigue according to the driving. The fatigue control module may preferably control an emission time when the light irradiation amount of the light source unit is configured as 1 to 4 J/cm$^2$ and preferably maximize the cell stimulation effect by setting the emission time within 20 minutes. However, the fatigue control module 230 preferably calculates a light intensity and an irradiation time according to a total irradiation energy amount.

Figure 6:
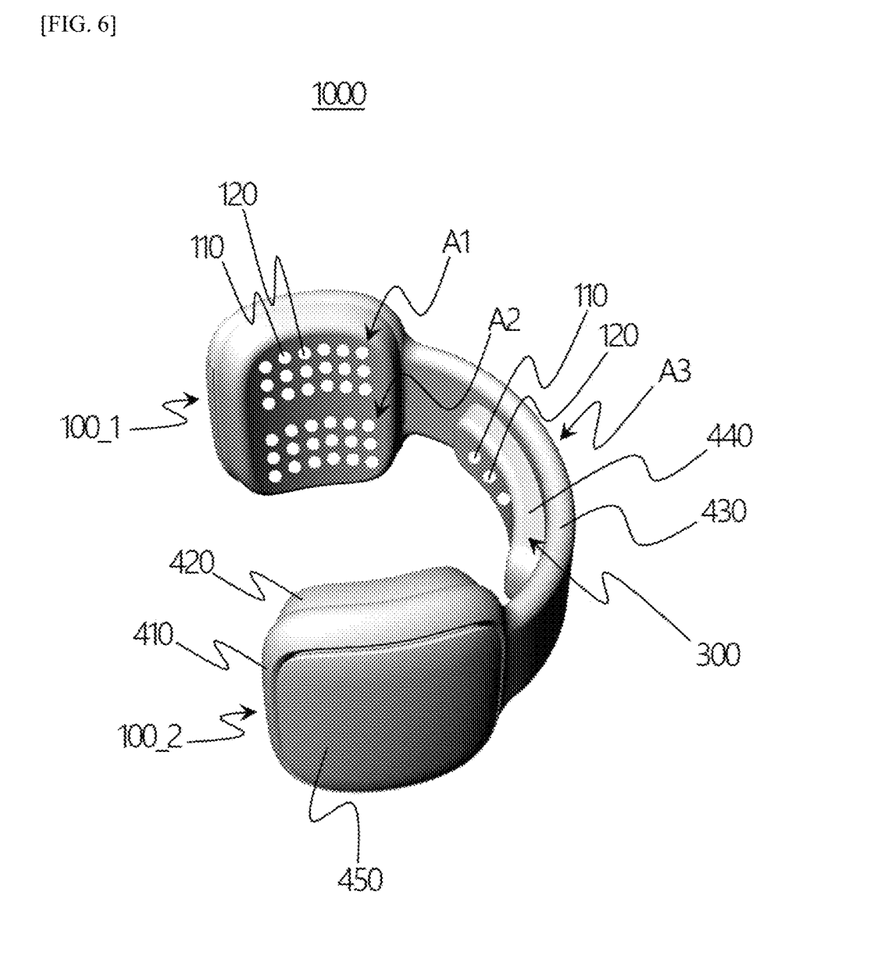
FIGS. 6 and 7 are rendering images of the stimulating device for the growth plate according to the embodiment of the present invention.
Figure 7:
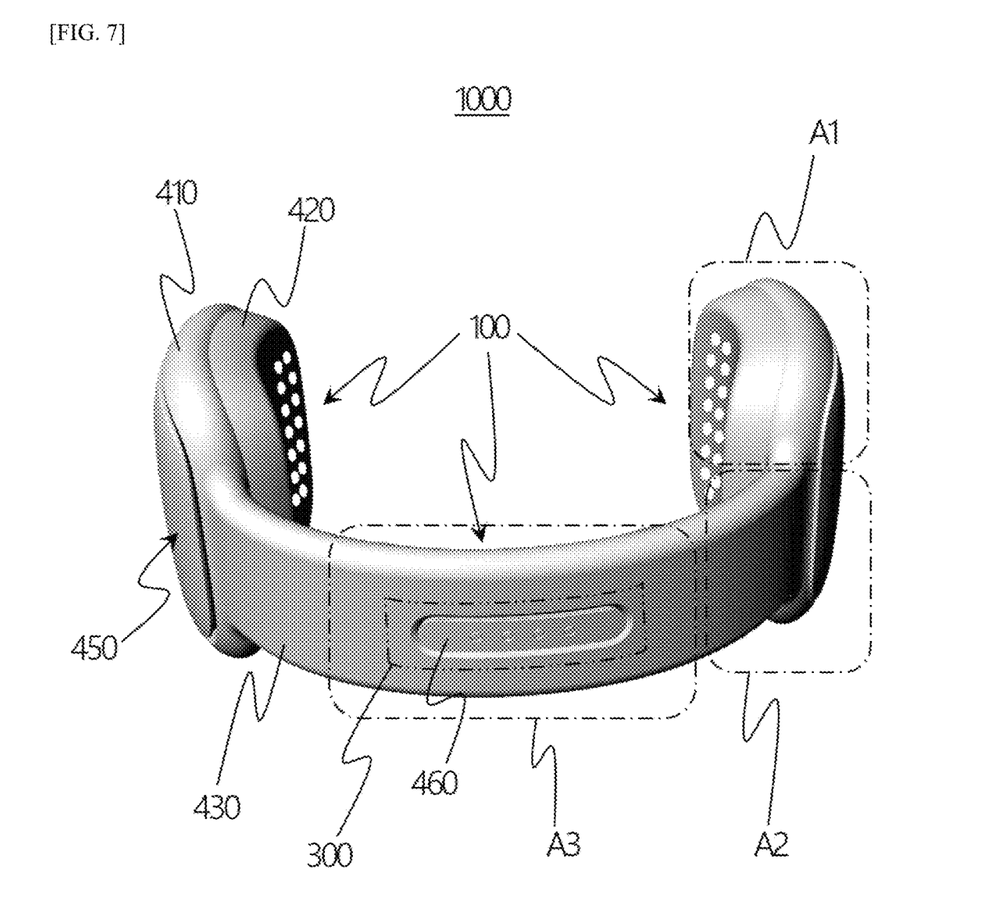
Figure 8:
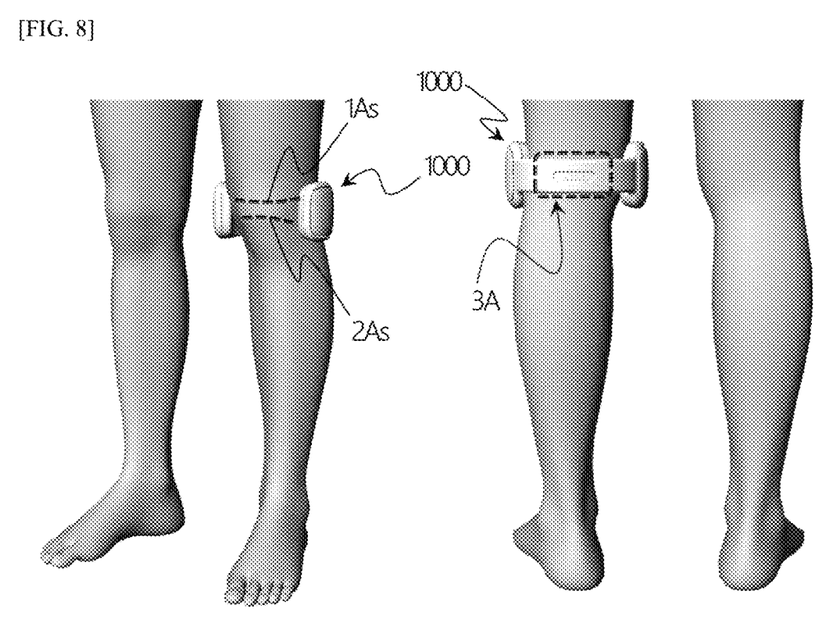
FIG. 8 is a diagram of describing a wearing example of the stimulating device for the growth plate according to the embodiment of the present invention.

Hereinafter, the stimulating device for the growth plate according to an embodiment of the present invention will be described in more detail. FIGS. 6 and 7 are rendering images of the stimulating device for the growth plate according to an embodiment of the present invention and FIG. 8 is a diagram of describing a wearing example of the stimulating device for the growth plate according to an embodiment of the present invention.

Referring to the drawings, in the stimulating device for the growth plate, two side pads 420 are attached to a side housing 410 for mounting and a rear housing 430 and a rear pad 440 are connected therebetween.

The light source unit 100 consists of a first module 100_1 having the same configuration installed in the side housing 410 and a second module 100_2 disposed to face the first module 100_1. This is to simulate the knee side surface where the growth plate is disposed at the knee.

At this time, light source devices are disposed at both the first module 100_1 and the second module 100_2. The light source devices apply the light to the first area A1 and the second area A2 at the same time. At this time, in order to concentrate the light in a growth plate A1s of the first area A1 and a growth plate A2s of the second area A2, the light source device may be disposed so that the light emission amounts of the upper and lower parts are larger than that of the center. For example, referring to FIG. 6, it can be seen that the light source device is not disposed between the first area and the second area. However, for design beauty, of course, the light source device may be evenly disposed evenly in a boundary area between the first area and the second area.

In this case, the vibration unit 300 is disposed and formed in the rear housing 430 so that the first module 100_1 and the second module 100_2 are connected to each other. Accordingly, in the first module 100_1 and the second module 100_2, the light may be applied to the first area A1 and the second area A2 and the vibration may be applied to the third area A3 at the same time.

Furthermore, the stimulating device for the growth plate is formed to continuously surround the first area, the second area, and the third area and a light path is opened and the front of the knee is formed by opening an optical path. Since the front of the knee is configured in the form of surrounding the patella, and the like, it is difficult to transmit the light, and as a result, the front of the knee is opened to prevent power waste. However, a fixing member for fixing the front of the knee may be used.

Meanwhile, the application of the light and vibration is to confirm the drive through an indicator 460 disposed in the rear surface, or the housing of other places, and a structure attached to a cover 450 is illustrated for replacing and inserting the power source, but of course, the present invention is not limited thereto.

FIG. 8 is a diagram of describing a wearing example of the stimulating device for the growth plate according to an embodiment of the present invention. As illustrated in FIG. 8, it can be seen that the stimulating device 1000 for the growth plate according to an embodiment of the present invention simultaneously emits the light to the growth plate A1s in the first area, the growth plate A2s in the second area, and the third area A3 and applies the vibration to the third area A3 at the same time.

As described above, preferred embodiments of the present invention have been disclosed in the present invention and the drawing and although specific terminologies are used, but they are used in a general meaning for easily describe the technical content of the present invention and help understanding the present invention and are not limited to the scope of the present invention. In addition to the embodiments disclosed herein, it is apparent to those skilled in the art that other modified examples based on the technical spirit of the present invention can be executed.

EXPLANATION OF REFERENCE NUMERALS AND SYMBOLS

1000: Stimulating device for growth plate
100: Light source unit
100_1: First module
100_2: Second module
110: Visible light emitting module
120: Non-visible light emitting module
200: Control unit
210: Emission control module
220: Fatigue control module
300: Vibration unit
410: Side housing
420: Side pad
430: Rear housing
440: Rear pad
450: Cover
460: Indicator
A1: First area
A2: Second area
A3: Third area
A1s: Growth plate of first area
A2s: Growth plate of second area

The invention claimed is:

1. A stimulating device for a growth plate comprising:
a single pair of side housings (410) configured to wrap around a femoral epiphysis area and a tibial epiphysis area;
a rear housing (430) connected to the pair of side housings (410) and configured to cover a rear of the knee,
wherein each side housing (410) has one end connected to the rear housing (430) and the other end configured as a free end, so that when the stimulating device is applied, a front of the knee is open, wherein a vertical width of each side housing is longer than a vertical width of the rear housing;
a single pair of side pads (420), each side pad attached to an inner surface of each side housing (410) and configured to directly contact the femoral epiphysis area and the tibial epiphysis area; and
a single rear pad (440) attached to an inner surface of the rear housing (430) and configured to directly contact a blood vessel area behind the knee, wherein a vertical width of each side pad is longer than a vertical width of the single rear pad,
wherein the vertical width of the single rear pad (440) is narrower than a vertical width of the rear housing (430) such that when the single rear pad (440) is configured to directly contact the blood vessel area behind the knee, the single rear pad is configured to protrude inward to support the behind the knee,
wherein each side housing (410) and the ear housing (430) include a light source unit (100) configured to emit light of 600 nm to 900 nm directly onto at least one of the femoral epiphysis area, the tibial epiphysis area, and the blood vessel area behind a knee,
wherein the light is simultaneously emitted to the femoral epiphysis area and the tibial epiphysis area.

2. The stimulating device for the growth plate of claim 1, wherein the light source unit further comprises a first module disposed in one side surface of the knee of the femoral epiphysis area and the tibial epiphysis area and a second module disposed at an opposite side surface to face the first module, wherein light source devices are disposed in the first module and the second module.

3. The stimulating device for the growth plate of claim 2, wherein in order to concentrate the light at the growth plates of the femoral epiphysis area and the tibial epiphysis area, the light source devices are disposed in the first module and the second module so that the light emission amounts of the upper and lower parts of the first module and the second module are larger than that of the center thereof.

4. The stimulating device for the growth plate of claim 1, wherein the light is emitted by a visible light emitting device and a non-visible light emitting device of the light source unit, the visible light emitting device configure to emit red light having a wavelength of 600 nm to 730 nm and the non-visible light emitting device configure to emit infrared light having a wavelength of 750 nm to 900 nm together.

5. The stimulating device for the growth plate of claim 1, further comprising:
a vibration unit located at the single rear pad and configured to apply vibration to any one of the femoral epiphysis area and the tibial epiphysis area.

6. The stimulating device for the growth plate of claim 5, wherein the vibration unit is applied to the blood vessel area behind the knee.

7. The stimulating device for the growth plate of claim 4, wherein the red light and the infrared light are simultaneously applied to the first area to the blood vessel area behind the knee.

8. The stimulating device for the growth plate of claim 5, wherein the vibration of the vibration unit and the light emission of the light source unit are alternately or simultaneously performed.

9. The stimulating device for the growth plate of claim 6, wherein the vibration unit for applying the vibration to the blood vessel area behind the knee is formed to connect the first module and the second module.

10. The stimulating device for the growth plate of claim 9, wherein the stimulating device for the growth plate is formed so that the front of the knee is opened.

11. The stimulating device for the growth plate of claim 5, wherein the stimulating device for the growth plate simultaneously applies the light and the vibration to the first area to the blood vessel area behind the knee.

* * * * *